United States Patent [19]

Schwan

[11] 3,969,355

[45] July 13, 1976

[54] 5-AMINOETHYL-2,4-DIPHENYLPYRIMIDINE DIHYDROBROMIDE

[75] Inventor: Thomas J. Schwan, Norwich, N.Y.

[73] Assignee: Morton-Norwich Products, Inc., Norwich, N.Y.

[22] Filed: Oct. 24, 1975

[21] Appl. No.: 625,751

Related U.S. Application Data

[62] Division of Ser. No. 520,024, Nov. 1, 1974, Pat. No. 3,944,581.

[52] U.S. Cl. ............... 260/256.4 R; 260/256.5 R; 424/251
[51] Int. Cl.² ........................................ C07D 239/26
[58] Field of Search ........................... 260/256.4 R

[56] References Cited
UNITED STATES PATENTS
3,658,817  4/1972  Orlando .................. 260/251 R OTHER PUBLICATIONS
Cherkasov, et al., "Chemical Abstracts", vol. 79, 1970, col. 43596c.

Primary Examiner—Nicholas S. Rizzo
Assistant Examiner—James H. Turnipseed
Attorney, Agent, or Firm—Anthony J. Franze

[57] ABSTRACT

Certain 5-substituted-2,4-diphenylpyrimidines of the formula:

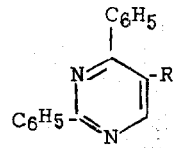

wherein R is acetyl, 1-hydroxy-1-ethyl, 1-amino-1-ethyl, 1-hydroxy-2-isopropylamino-1-ethyl, 5,6-dihydroimidazo [2,1-b] thiazol-3-yl, 2-amino-1-hydroxy-1-ethyl, and 1-hydroxy-2-phthalimido-1-ethyl possess pharmacological activity as anticonvulsant agents.

1 Claim, No Drawings

5-AMINOETHYL-2,4-DIPHENYLPYRIMIDINE DIHYDROBROMIDE

This is a division of application Ser. No. 520,024, filed November 1, 1974 now U.S. Patent No. 3,944,581.

This invention relates to chemical compounds. In particular it is concerned with compounds of the formula:

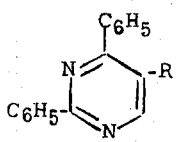

wherein R is acetyl, 1-hydroxyl-1-ethyl, 1-amino-1-ethyl, 1-hydroxy-2-isopropylamino-1-ethyl, 5,6-dihydromidaze[2,1-b]thiazol-3-yl, 2-amino-1-hydroxy-1-ethyl, and 1-hydroxy-2-phthalimido-1-ethyl. The compounds of this invention possess pharmacological activity affecting the central nervous system. When administered perorally to mice they exhibit anticonvulsant action. Their anticonvulsant property is evidenced in the control of pentylenetetrazol induced convulsions. When administered orally in doses ranging from 50–200 mg/kg in 0.5 percent aqueous methyl cellulose to mice intravenously receiving 45 mg/kg of pentylenetetrazol, these compounds counteract the convulsive property of pentylenetetrazol.

In order that this invention may be readily available to and understood by those skilled in the art the following examples are appended:

EXAMPLE I

A. 2-Ethoxymethylene-1-phenyl-1, 3-butanedione

To 200 g (1.23 moles) of benzoylacetone was added 320 g (2.16 moles) of ethyl orthoformate followed by 360 g (3.52 moles) acetic anhydride. The mixture was stirred and refluxed for 3.0 hours and the pot temperature dropped from 120° to 100° during the reflux period. The reflux condenser was removed and the volatile products were distilled at pot temperatures up to 140°. The remaining acetic anhydride and ethyl orthoformate were removed on a rotary evaporator at 100°. The residue crystallized at room temperature was recrystallized from toluene to give in two crops 206 g (77%) of the product, m.p. 68°–71°.

The analytical sample, m.p. 68°–71°, was obtained by recrystallization from toluene.

Anal. Calcd. for $C_{13}H_{14}O_3$: C, 71.54; H, 6.47. Found: C, 71.65; H, 6.47.

B. 2,4-Diphenyl-5-pyrimidyl Methyl Ketone

To 1500 ml of methanol stirred at room temperature was added quickly 108 g (2.0 moles) of sodium methoxide. The solution was allowed to stand at ambient temperature for 90 min, then cooled to 15° while 348 g (2.0 moles) of benzamidine hydrochloride monohydrate was added quickly with vigorous stirring. While the mixture was initially cooled and stirred at 0°, a solution of 436 g (2.0 moles) of A in 800 ml methanol was added over 30 minutes. The mixture was stirred at ambient temperature for 18 hours, then stirred and refluxed for an additional 4 hours before methanol (2200 ml) was distilled off at atmospheric pressure. Chloroform (1000 ml) and water (500 ml) were added to the residue and the mixture was stirred at ambient temperature for 20 minutes.

The organic layer was separated and the aqueous layer was extracted with 150 ml portions of chloroform. The combined organic extracts were washed with 500 ml water, dried (MgSO₄), and concentrated to dryness in vacuo to give 562 g of an oily residue which crystallized at room temperature.

The residue was dissolved in 1600 ml boiling ethanol and the solution was stored at ambient temperature 30 minutes. The mixture was allowed to stand at ambient temperature for 15 hours and then filtered. The crystalline product was washed with 250 ml ethanol, and air dried to give 254 g (46%) of 2,4-diphenyl-5-pyrimidyl methyl ketone m.p. 100°–108°.

An analytical sample of 2,4-diphenyl-5-pyrimidyl methyl ketone, m.p. 107°–110°, was obtained by recrystallization from ethanol.

Anal. Calcd. for $C_{18}H_{14}N_2O$: C, 78.81; H, 5.14; N, 10.21. Found: C, 78.46; H, 5.11; N, 10.15.

The filtrate and washings from the isolation of the product were concentrated to 1600 ml, allowed to cool to room temperature, and seeded. The mixture was allowed to stand at ambient temperature for 24 hours and filtered. An additional 6.3 g of 2,4-diphenyl-5-pyrimidyl methyl ketone was obtained.

Additional standing at room temperature for 80 hours gave 5.20 g of a mixture of the ketone and 2-phenyl-4-methyl-5-pyrimidyl phenyl ketone.

The filtrate was concentrated to 500 ml in a stainless steel beaker. The solution was cooled to room temperature. The mixture was stored at room temperature for 72 hours. The solid was filtered, washed with three 100 ml portions of ethanol, and air dried to give 212 g of solid product.

Recrystallization of the product from 500 ml absolute ethanol gave 157 g (29%) of 2-phenyl-4-methyl-5-pyrimidyl phenyl ketone.

An analytical sample, m.p. 68°–72°, was obtained by recrystallization from absolute ethanol.

Anal. Calcd. for $C_{18}H_{14}N_2O$: C, 78.81; H, 5.14; N, 10.21. Found: C, 78.64; H, 5.18; N, 10.29.

EXAMPLE II

α-Methyl-2,4-diphenyl-5-pyrimidinemethanol

To a mixture of 41.1 g (0.15 mole) of 2,4-diphenyl-5-pyrimidyl metyl ketone in 500 ml methanol stirred at 5°–10° was added over 20 minutes 11.4 g (0.30 mole) sodium borohydride. The resulting solution was stirred at 5°–10° for 30 minutes and then stirred at ambient temperatures for 2 hours. The solvents were removed in vacuo and the residue was partitioned between 500 ml CHCl₃ and 500 ml water. The aqueous layer was extracted with two 500 ml portions of CHCl₃. The combined CHCl₃ extracts were washed with 250 ml water, dried (MgSO₄), and concentrated to dryness in vacuo.

Crystallization from 100 ml toluene gave, in two crops, 34 g (82%) of the carbinol, m.p. 108°–113°. Recrystallization from heptane gave an analytical sample, m.p. 110°–113°.

Anal. Calcd. for $C_{18}H_{16}N_2O$: C, 78.23; H, 5.28; N, 10.14. Found: C, 78.39; H, 5.90; N, 10.06.

EXAMPLE III

A. α-{[(2,4-Diphenyl-5-pyrimidinyl)-1-ethylidene]aminomethyl} benzyl Alcohol

A mixture of 61.2 g (0.223 mole) of 2,4-diphenyl-5-pyrimidyl methyl ketone, 30.6 g (0.223 mole) of β-hydroxphenethylamine and 3.0 g p-toluenesulfonic acid monohydrate in 750 ml toluene was stirred and refluxed using a Dean-Stark apparatus for 11.0 hours, amt. H$_2$O evolved: 4:10 ml; theoretical amt.: 4.0 ml. The toluene was removed in vacuo and the residue was dissolved in 1000 ml chloroform. The solution was washed with 300 ml H$_2$O, dried (MgSO$_4$), and concentrated to dryness in vacuo. Recrystallization of the residue from ethanol gave in three crops 72 g (82%) of the product, m.p. 140°–144°. ; N, Anal. Calcd. for C$_{26}$H$_{23}$N$_3$O: C, 79.36; H, 5.90: N, 10.68. Found: C, 79.64; H, 5.91; N, 10.70.

B. 5-{1-[(β-Hydroxyphenethyl)amino]ethyl}-2,4-diphenylpyrimidine Hydrochloride

To a suspension of 64.8 g (0.165 mole) of A in 1000 ml CH$_3$OH stirred at 5°–10° was added over 5 min 12.54 g (0.33 mole) of sodium borohydride. The solution was stirred at 5°–10° for 1 hour and then stirred at ambient temperatures for 16 hours.

The solution was stripped and the residue was partitioned between 300 ml CHCl$_3$ and 300 ml H$_2$O. The aqueous layer was extracted with two 100 ml portions of CHCl$_3$ and the combined CHCl$_3$ extracts were washed with 200 ml H$_2$O, dried (MgSO$_4$), and concentrated to dryness in vacuo.

The residue was dissolved in 190 ml boiling isopropanol. To the cooled solution was added 100 ml CH$_3$OH saturated with HCl. The mixture was stored at 0° for 20 hours, the solid filtered, washed with two -50 ml portions of isopropanol, and air dried to give 57.0 g (80%) of product, m.p. 214°–219°. An analytical sample, m.p. 221°–227°, was obtained by recrystallization from acetonitrile.

Anal. Calcd. for C$_{26}$H$_{25}$N$_3$O.HCl: C, 72.29; H, 6.07; N, 9.78. Found: C, 72.27; H, 6.18; N, 9.81.

C. 1-(2,4-Diphenyl-5-pyrimidyl) ethylamine Dihydrobromide

A mixture of 40.0 g (0.093 mole) of B and 400 ml 48% HBr was stirred and refluxed at 125°–126°for 3.5 hours. The mixture was then cooled and stirred in an ice-bath for 30 minutes and the solid was filtered using a medium sintered glass funnel. The solid was washed with four 100 ml portions of ethyl acetate and air dried to give 35.3 g (87%) of the product, m.p. 294°–296°. An analytical sample, m.p. 293°–296°, was obtained by recrystallization from absolute ethanol-ethyl acetate.

Anal. Calcd. for C$_{18}$H$_{17}$N$_3$.2HBr: C, 49.45; H, 4.38; N, 9.61. Found: C, 49.89; H, 4.61; N, 9.49.

EXAMPLE IV

A. 2,4-Diphenyl-5-pyrimidyl bromomethyl ketone

An 86 g (0.31 mole) portion of 2,4-diphenyl-5-pyrimidyl methyl ketone in 1.1 l of dioxane was treated with 136 g (0.61 mole) of cupric bromide using rapid stirring. The reaction mixture was stirred for 15 at ambient temperature, refluxed for 3 hours, cooled, stirred for 2 additional hours and filtered. The off-white solid was washed with two 300 ml portions of chloroform. The filtrate and washings were combined and concentrated to dryness under reduced pressure to give a gray crystalline solid.

The crude product was recrystallized from 2 l of absolute ethanol to give an off-white solid which was washed with 200 ml of absolute ethanol and air dried, m.p. 131°–133°. Yield 57 g (52%).

B. α-Bromomethyl-2,4-diphenyl-5-pyrimidinemethanol

To a suspension of 71 g (0.20 mole) of A in 1.5 l of anhydrous methanol was added 15.2 g (0.40 mole) of sodium borohydride at 10°–15° using rapid stirring over 0.3 hours. The reaction mixture was stirred at ambient temperature for 2.3 hours and poured with rapid stirring into 2.5 l of cold (10°–15°) water. The hydrolysis mixture was extracted with one 2 l and two 500 ml portions of chloroform, dried over magnesium sulfate and filtered. The filtrate was concentrated under reduced pressure to give 67.5 g (95%) of the crude product, a viscous yellow-orange oil.

C. α-(Isopropylaminomethyl)-2,4-diphenyl-5-pyrimidinemethanol hydrochloride

A 67.5 g (0.19 mole) portion of B in 150 ml of isopropylamine was treated with 26.2 g (0.19 mole) of K$_2$CO$_3$ and 24.0 g (0.14 mole) of KI. The reaction mixture was refluxed gently using a water bath, at 40°–42°, for 24 hours, stored overnight at room temperature and concentrated under reduced pressure. The residue was taken up in 1.5 l of water, stirred and extracted with 1.2 l of chloroform. The extract was washed with 1 l of water, dried over MgSO$_4$ overnight, filtered and concentrated under reduced pressure to give 72 g of a crude light brown oil which crystallized, m.p. 86°–95°.

The crude free base was taken up in 300 ml of isopropanol and adjusted to pH$_2$ with 400 ml of methanolic HCl. The acidified solution was filtered and concentrated to dryness to give 74 g of the crude hydrochloride, a light brown solid, m.p. 193°–197°.

The crude hydrochloride was recrystallized from 600 ml of ethanol, washed with ethaol-ether and air dried, m.p. 207°–208°dec. Yield: 40 g (57%).

An analytical sample, m.p. 203°–206°, was recrystallized from acetonitrile.

Anal. Calcd. for C$_{21}$H$_{23}$N$_3$O.HCl: C, 68.19; H, 6.54; N, 11.36. Found: C, 67.90; H, 6.59; N, 11.30.

EXAMPLE V 5,6-Dihydro-3-(2,4-diphenyl-5-pyrimidyl)imidazo[2,1-b]thiazole Hydrobromide A 21.1 g (0.060 mole) portion of the compound of Example IV-A in 250 ml of ethanol was treated with 6.1 g (0.060 mole) of ethylenethiourea using rapid stirring. The reaction mixture was refluxed for 5 hours, stored overnight at room temperature, cooled 2 hours with stirring and filtered. The solid was washed with 25 ml of ethanol, ether and air dried, m.p. 290°–292° dec. Yield: 22 g (86%).

The analytical sample, m.p. 292°–294° dec., was recrystallized from ethanol.

Anal. Calcd. for C$_{21}$H$_{16}$N$_4$S.HBr: C, 57.67; H, 3.92; N, 12.81. Found: C, 57.55; H, 4.03; N, 12.74.

EXAMPLE VI

α-(Phthalimidomethyl)-2,4-diphenyl-5-pyrimidinemethanol

A 33.5 g (0.095 mole) portion of the compound of Example IV-B in 430 ml of dimethyl sulfoxide was treated with 19.2 g (0.104 mole) of potassium phthalimide and heated with stirring at 90°–95° for 20 hours. The reaction mixture was poured into 3 l of cold tap water, warmed to 35°, stirred for 2 hours and filtered. The cream colored solid was washed with 800 ml of water, air dried and dried to a constant weight at 60°, m.p. 149°–159°. Yield: 37 g (93%).

The crude product was recrystallized from 1 l of ethanol, washed with 100 ml of ethanol and air dried to give 27 g (68%) of a cream colored solid, m.p. 178°–180°.

An analytical sample, m.p. 179°–180° was recrystallized from ethanol.

Anal. Calcd. for $C_{26}H_{19}N_3O_3$: C, 74.09; H, 4.54; N, 9.97. Found: C, 73.65; H, 4.49; N, 9.91.

EXAMPLE VII

α-Aminomethyl-2,4-diphenyl-5-pyrimidinemethanol hydrochloride

A 40 g (0.095 g) portion of the compound of Example VI in 1.2 l of ethanol was treated with 120 ml of 85% hydrazine hydrate. The reaction mixture was refluxed for 18 hours. The slurry was cooled to room temperature, acidified with 1.3 l of 10% HCl, refluxed for 2 hours, cooled to 30° and adjusted to pH 9-10 with 1.4 l of 10% NaOH. The basic aqueous mixture was extracted with five 1 l portions of chloroform. The chloroform extracts were washed with four 1 l portions of $H_2O$, dried over $MgSO_4$ for 3 hours, filtered and concentrated under reduced pressure to give 25.5 g (93%) of the crude, light yellow, base (free), m.p. 129°–134°.

The crude free base was taken up in 150 ml of warm methanol and adjusted to pH 2-3 with methanolic HCl. The solution was concentrated to dryness under reduced pressure leaving 28.5 g (92%) of the hydrochloride, a light yellow solid, m.p. 223°–227° dec.

The crude product was boiled with 200 ml of ethyl acetate for 20 min. The slurry was filtered, washed with an additional 100 ml of ethyl acetate, and air dried, m.p. 227°–230° dec. Yield: 23.5 g (76%).

An analytical sample, m.p. 242°–243° dec., was recrystallized from ethyl acetate-isopropanol (2:1).

Anal. Calcd. for $C_{18}H_{17}N_4O \cdot HCl$: C, 65.95; H, 5.53; N, 12.82. Found: C, 65.66; H, 5.62; N, 12.97.

What is claimed:

1. The compound 1-(2,4-diphenyl-5-pyrimidyl)ethylamine dihyrobromide.